(12) United States Patent
Cheng et al.

(10) Patent No.: US 10,791,935 B2
(45) Date of Patent: Oct. 6, 2020

(54) METHOD AND DEVICE FOR DYNAMICALLY ADJUSTING FLUORESCENT IMAGING

(71) Applicant: Quanta Computer Inc., Taoyuan (TW)

(72) Inventors: Kai-Ju Cheng, Taoyuan (TW);
Hsin-Lun Hsieh, Taoyuan (TW);
Chin-Yuan Ting, Taoyuan (TW);
Tsung-Hsin Lu, Taoyuan (TW)

(73) Assignee: QUANTA COMPUTER INC., Guishan Dist., Taoyuan (TW)

( * ) Notice: Subject to any disclaimer, the term of this patent is extended or adjusted under 35 U.S.C. 154(b) by 99 days.

(21) Appl. No.: 16/157,312

(22) Filed: Oct. 11, 2018

(65) Prior Publication Data
US 2019/0350461 A1    Nov. 21, 2019

(30) Foreign Application Priority Data
May 17, 2018  (TW) .............................. 107116766 A

(51) Int. Cl.
*A61B 6/14*    (2006.01)
*A61B 5/00*    (2006.01)
(Continued)

(52) U.S. Cl.
CPC ............ *A61B 5/0088* (2013.01); *A61B 1/045* (2013.01); *A61B 1/24* (2013.01); *A61B 5/0071* (2013.01); *H04N 5/2352* (2013.01)

(58) Field of Classification Search
CPC . H01L 2224/48091; H01L 2924/00014; H01L 25/167; A61B 1/045; A61B 1/0684;
(Continued)

(56) References Cited

U.S. PATENT DOCUMENTS

| 6,051,826 A | 4/2000 | Arimoto et al. |
| 8,050,519 B2 | 11/2011 | Katsumata et al. |

(Continued)

FOREIGN PATENT DOCUMENTS

| CN | 101331519 A | 12/2008 |
| CN | 101528116 A | 9/2009 |

(Continued)

OTHER PUBLICATIONS

Japanese language office action dated Jan. 21, 2020, issued in application No. JP2018-241549.
(Continued)

*Primary Examiner* — Irakli Kiknadze
(74) *Attorney, Agent, or Firm* — McClure, Qualey & Rodack, LLP

(57) ABSTRACT

A method for dynamically adjusting fluorescent imaging is provided. The method is used in a device and includes the following steps: emitting, by a light emitting diode, light to illuminate teeth in an oral cavity, wherein the light is used to generate fluorescence from the teeth; filtering, by an optical filter, the fluorescence; receiving, by an image sensor, a signal and adjusting a gain value of an analog-to-digital converter according to the signal; converting, by the analog-to-digital converter, the filtered fluorescence into a digital signal and adjusting the digital signal according to the gain value; and generating, by a processor, an output image signal that corresponds to the gain value from the digital signal.

8 Claims, 5 Drawing Sheets
(2 of 5 Drawing Sheet(s) Filed in Color)

(51) Int. Cl.
*A61B 1/045* (2006.01)
*A61B 1/24* (2006.01)
*H04N 5/235* (2006.01)

(58) Field of Classification Search
CPC ....... A61B 1/24; A61B 5/0071; A61B 5/0088;
A61B 2560/0214; A61B 2560/0456;
A61B 5/0084; A61B 5/6887; A61B 5/00;
A61B 5/4547; A61B 5/682; A61B 1/043;
A61B 2560/0223; A61B 5/7257; A61B
1/0061; A61B 1/07; A61B 5/0075; A61B
1/00009; A61B 1/0638; A61B 1/0646;
A61B 1/0669; A61B 1/00186; A61B
1/00059; A61B 1/05; A61B 1/0653; A61B
1/0005; A61B 1/0051; A61C 1/088; A61C
3/02; A61C 19/04; A61C 17/225; A61C
17/34; H04N 5/2352; H04N 2005/2255;
H04N 5/2256; H04N 5/33; H04N 5/225;
H04N 13/344; H04N 13/398; H04N
5/23293; H04N 5/2354; H04N 5/332;
A46B 15/0034; A46B 2200/1066; A46B
15/00; A46B 15/0036; A46B 9/04; G01N
2021/6421; G01N 21/64; G01N 21/6486;
G01N 2035/00376; G01N 2035/0405;
G01N 21/0332; G01N 35/0099; G01N
21/6456; G01N 2021/6439; G01N
2021/6491; G01N 1/10; G01N 1/20;
G01N 1/38; G01N 2001/1031; G01N
21/76; G01N 33/4833; G01N 33/487;
G01N 33/582
USPC ................................................... 250/363.02
See application file for complete search history.

(56) References Cited

U.S. PATENT DOCUMENTS

| | | | |
|---|---|---|---|
| 8,314,377 | B2 | 11/2012 | Binner |
| 8,363,912 | B2 | 1/2013 | Thoms |
| 8,702,422 | B2 | 4/2014 | Binner et al. |
| 9,544,518 | B2 | 1/2017 | Awatani et al. |
| 10,070,791 | B2 | 9/2018 | Liang et al. |
| 2002/0177751 | A1* | 11/2002 | Ueno ................ A61B 1/045 600/160 |
| 2012/0147166 | A1* | 6/2012 | Minetoma .......... A61B 1/00009 348/68 |
| 2014/0221745 | A1* | 8/2014 | Yamaguchi ........... H04N 9/045 600/109 |
| 2016/0287084 | A1* | 10/2016 | Vermeulen .......... A61B 5/0088 |

FOREIGN PATENT DOCUMENTS

| | | |
|---|---|---|
| CN | 101636106 A | 1/2010 |
| CN | 102106720 A | 6/2011 |
| EP | 1462176 A2 | 9/2004 |
| JP | 2006-271869 A | 10/2006 |
| JP | 2008-86554 A | 4/2008 |
| JP | 2009095538 A | 5/2009 |
| JP | 2015-119385 A | 6/2015 |
| WO | 2015082390 A1 | 6/2015 |

OTHER PUBLICATIONS

English language translation of office action.
Chinese language office action dated Dec. 26, 2018, issued in application No. TW 107116766.
EP Extended Search Report dated Jul. 15, 2019 for corresponding application No. 18209318.7 in Europe, pp. 1-9.
Chinese language office action dated Apr. 15, 2019, issued in application No. TW 107116766.

* cited by examiner

METHOD AND DEVICE FOR DYNAMICALLY ADJUSTING FLUORESCENT IMAGING

CROSS REFERENCE TO RELATED APPLICATIONS

This application claims priority of Taiwan Patent Application No. 107116766, filed on May 17, 2018, the disclosure of which is incorporated by reference herein in its entirety.

BACKGROUND OF THE INVENTION

Field of the Invention

The present disclosure relates to a method and device for dynamically adjusting fluorescent imaging. Specifically, the present disclosure relates to a method and device for dynamically adjusting fluorescent imaging to detect dental plaque on teeth.

Description of the Related Art

Caries and periodontal diseases are thought to be infectious diseases caused by bacteria in dental plaque. Removal of dental plaque is very important for the health of teeth and prevention of cavities. Dental plaque is not easy to identify with the naked eye, however. Therefore, a variety of plaque detection apparatuses have been produced to aid in the detection of dental plaque and/or caries.

Most dental plaque detection apparatuses make use of the fact that the visible luminescence spectra of dental plaque (and/or caries) and non-decayed regions of a tooth are substantially different. For example, one well-known type of dental plaque apparatus utilizes irradiated light to illuminate tooth material and gums to identify areas infected with dental plaque. This type of plaque detection apparatus may utilize a blue excitation light to illuminate the tooth surface and may be configured with a filter that filters blue light including a wavelength less than about 480 nanometers (nm) to reveal regions affected by dental plaque and/or caries.

However, when the filter of the type of apparatus is determined, the fluorescent imaging produced by the apparatus may not change. Therefore, there is a need for a method and device for dynamically adjusting fluorescent imaging to improve the disadvantages.

BRIEF SUMMARY OF THE INVENTION

The following summary is illustrative only and is not intended to be limiting in any way. That is, the following summary is provided to introduce concepts, highlights, benefits and advantages of the novel and non-obvious techniques described herein. Select, not all, implementations are described further in the detailed description below. Thus, the following summary is not intended to identify essential features of the claimed subject matter, nor is it intended for use in determining the scope of the claimed subject matter.

A method and device for dynamically adjusting fluorescent imaging are provided.

In a preferred embodiment, a method for dynamically adjusting fluorescent imaging is provided in the disclosure. The method is used in a device and includes the following steps: emitting, by a light emitting diode, light to illuminate teeth in an oral cavity, wherein the light is used to generate fluorescence from the teeth; filtering, by an optical filter, the fluorescence; receiving, by an image sensor, a signal and adjusting a gain value of an analog-to-digital converter according to the signal; converting, by the analog-to-digital converter, the filtered fluorescence into a digital signal and adjusting the digital signal according to the gain value; and generating, by a processor, an output image signal that corresponds to the gain value from the digital signal.

In some embodiments, the image sensor adjusts the gain value that corresponds to a blue light channel of the analog-to-digital converter according to the signal.

In some embodiments, the optical filter filters out light including a wavelength band that is less than about 450 nanometers (nm).

In some embodiments, the optical filter filters out light not including wavelength bands selected from the ranges of 430 nm to 480 nm, 620 nm to 750 nm and combinations thereof.

In some embodiments, the optical filter filters out light not including wavelength bands in the range from 450 nm to 680 nm.

In a preferred embodiment, a device for dynamically adjusting fluorescent imaging is provided in the disclosure. The device comprises a light emitting diode, an optical filter, an image sensor and a processor. The light emitting diode emits light to illuminate teeth in an oral cavity, wherein the light is used to generate fluorescence from the teeth. The optical filter filters the fluorescence. The image sensor coupled to the optical filter and receiving a signal comprises an analog-to-digital converter. The analog-to-digital converter converts the filtered fluorescence into a digital signal. The processor is coupled to the image sensor and generates an output video signal from the digital signal. The image sensor adjusts a gain value of the analog-to-digital converter according to the signal. The analog-to-digital converter adjusts the digital signal according to the gain value, so that the processor generates an output image signal that corresponds to the gain value.

BRIEF DESCRIPTION OF DRAWINGS

The accompanying drawings are included to provide a further understanding of the disclosure, and are incorporated in and constitute a part of the present disclosure. The drawings illustrate implementations of the disclosure and, together with the description, serve to explain the principles of the disclosure. It should be appreciated that the drawings are not necessarily to scale as some components may be shown out of proportion to the size in actual implementation in order to clearly illustrate the concept of the present disclosure.

The patent or application file contains at least one drawing executed in color. Copies of this patent or patent application publication with color drawing(s) will be provided by the Office upon request and payment of the necessary fee.

DETAILED DESCRIPTION OF THE INVENTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects. Furthermore, like numerals refer to like elements throughout the several views, and the articles "a" and "the" includes plural references, unless otherwise specified in the description.

It should be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

Figure 1:
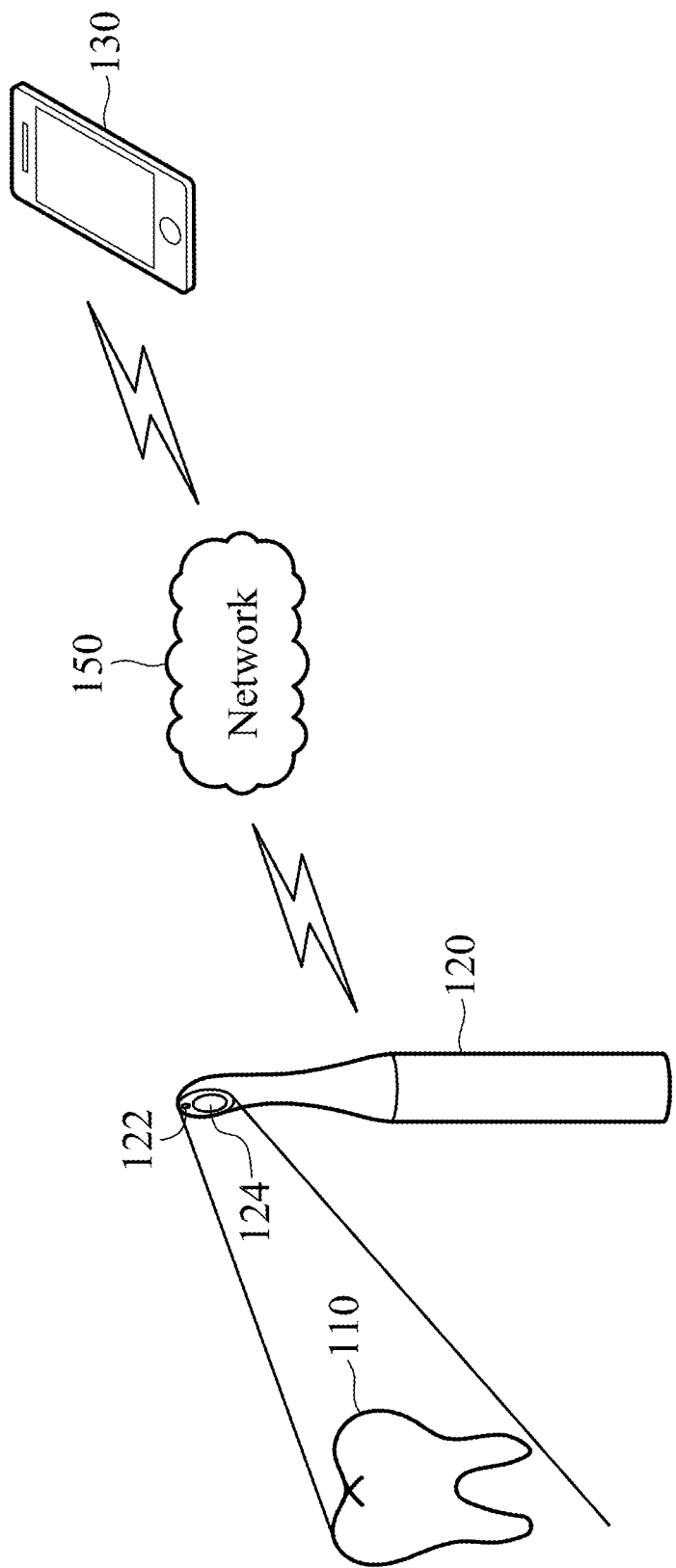
FIG. 1 is a schematic diagram illustrating an operation of examining teeth by an examining device in accordance with an embodiment of the present disclosure.

FIG. 1 is a schematic diagram illustrating an operation of examining teeth 110 by an examining device 120 in accordance with an embodiment of the present disclosure. In FIG. 1, the examining device 120 may at least comprise a light emitting diode 122, an optical filter 124 and an image sensor and a processor (not shown) that can be integrated into the examining device 120.

In some embodiments, the light emitting diode 122 can emit light including wavelength bands in the range from 370 nanometers (nm) to 430 nm to illuminate the teeth 110 in the oral cavity. In another embodiment, the light emitting diode 122 can emit light including a wavelength of 405 nm. Specifically, dental plaque on teeth 110 generate fluorescent emissions when the teeth 110 are illuminated with incident blue light of a particular wavelength.

The optical filter 124 is used to filter the fluorescence. The image sensor may be coupled to the optical filter 124, receives and converts the filtered fluorescence into a digital signal. The processor may be coupled to the image sensor and generates an output image signal from the digital signal.

The examining device 120 can be connected to an electronic device 130 using the network 150 to transmit the output image signal to the electronic device 130. Exemplary electronic devices may include a desktop computer, a notebook, a smart phone, a personal digital assistant (PDA), a tablet, or any other device having a display screen. The user may view the dental plaque on the teeth 110 in the output image signal through the electronic device 130. The network 150 can provide wired and/or wireless networks. The network 150 may also include a local area network (LAN) (e.g., an intranet), a wireless local area network (WLAN) or a Wi-Fi network, a third generation (3G) or a fourth generation (4G) mobile telecommunications network, a wide area network (WAN), the Internet, Bluetooth, or any suitable combination thereof.

In the embodiment, the examining device 120 is integrated with the light emitting diode 122 into a single device. The examining device 120 integrated into the single device may be separated from the light emitting diode 122. It should be noted that the examining device 120 may be a general electronic device such as a dental mirror or the like. Although the examining device 120 of FIG. 1 is shown in the form of a dental mirror, it should be understood by those skilled in the art that the present disclosure is not limited thereto.

Figure 2:
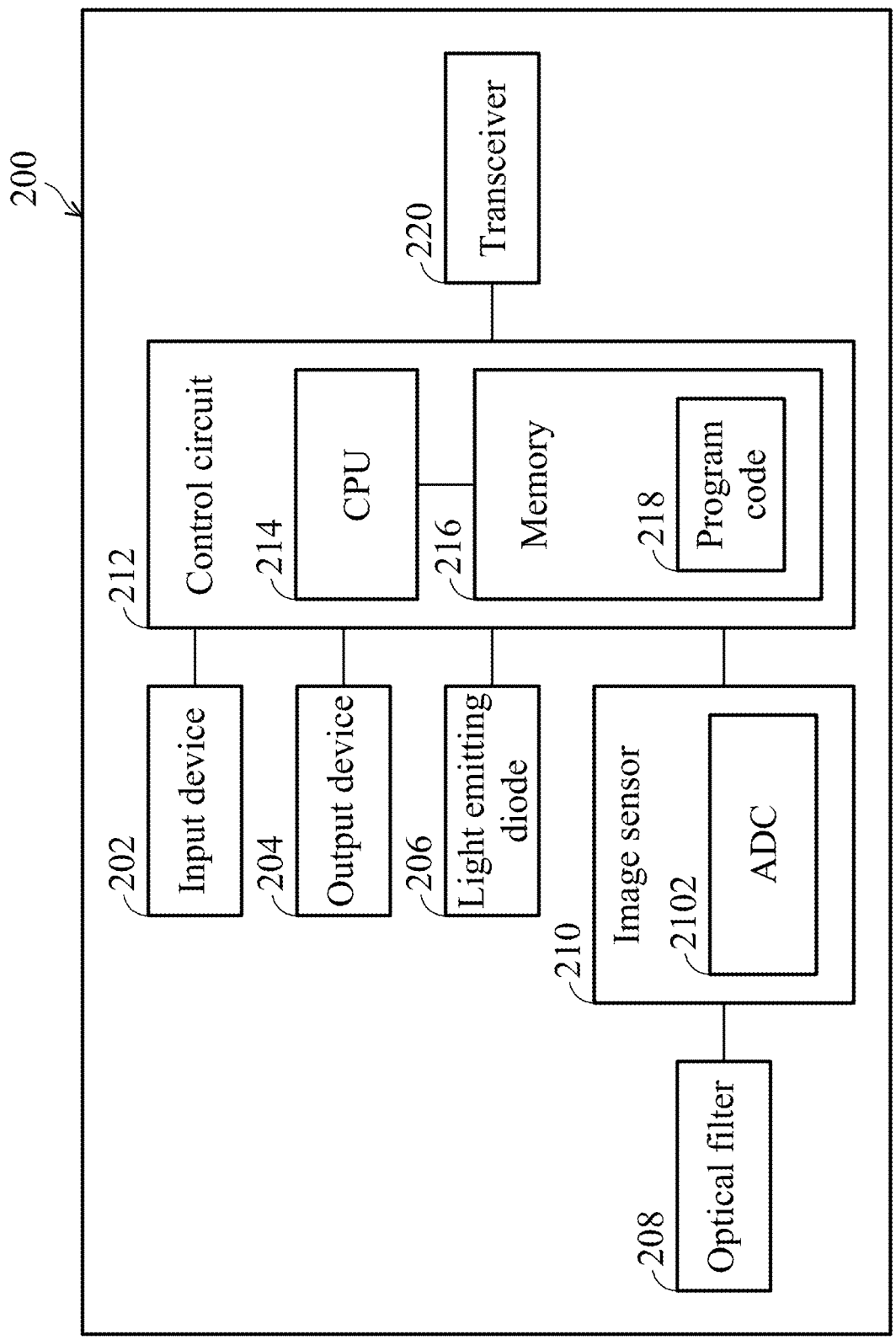
FIG. 2 is a simplified functional block diagram of an examining device according to one embodiment of the present disclosure.

FIG. 2 is a simplified functional block diagram of an examining device 200 according to one embodiment of the present disclosure. As shown in FIG. 2, the examining device 200 can be the examining device 120 of FIG. 1.

In FIG. 2, the examining device 200 may include an input device 202, an output device 204, a light emitting diode 206, an optical filter 208, an image sensor 210, a control circuit 212 and a transceiver 220. The image sensor 210 can at least comprise an analog-to-digital converter (ADC) 2102. The control circuit 212 can comprise a central processing unit (CPU) 214 and a memory 216.

The examining device 200 can receive signals input by a user through the input device 202, (such as a button) and can output images through the output device 204. In an embodiment, the light emitting diode 206 can emit light including wavelength bands in the range from 370 nm to 430 nm when energized. In another embodiment, the light emitting diode 122 can emit light including a wavelength of 405 nm. The light mentioned above may effectively generate detectable fluorescent emissions between normal dental tissue and abnormal dental tissue.

The optical filter 208 is used to filter the fluorescence. In one embodiment, the optical filter 208 filters out light including a wavelength band that is less than about 450 nm. In another embodiment, the optical filter 208 can filter out light not including wavelength bands selected from the ranges of 430 nm to 480 nm, 620 nm to 750 nm and combinations thereof. In yet another embodiment, the optical filter 208 filters out light not including wavelength bands in the range from 450 nm to 680 nm.

The image sensor 210 is coupled to the optical filter 208, receives the filtered fluorescence from the optical filter 208, and converts the filtered fluorescence into a digital signal by using the analog-to-digital converter 2102. In addition, the image sensor 210 can receive the signal input by the user through the input device 202 or the transceiver 220 to adjust a gain value of the analog-to-digital converter 2102. The analog-to-digital converter 2102 adjusts the digital signal according to the gain value, and transmits the adjusted digital signal to the control circuit 212. The CPU 214 in the control circuit 212 generates an output video signal that corresponds to the gain value after receiving the adjusted digital signal. Specifically, the image sensor 210 adjusts the gain value that corresponds to a blue light channel of the analog-to-digital converter 2102 according to the signal input by the user to change the strength of the signal of the blue light in the output image signal.

The memory 216 can store a program code 218. The control circuit 212 executes the program code 218 in the memory 216 through the CPU 214, thereby controlling the operation performed by the examining device 200. The transceiver 220 is used to receive and transmit wireless signals, delivering received signals to the control circuit 212, and outputting signals generated by the control circuit 212 wirelessly.

Figure 3:
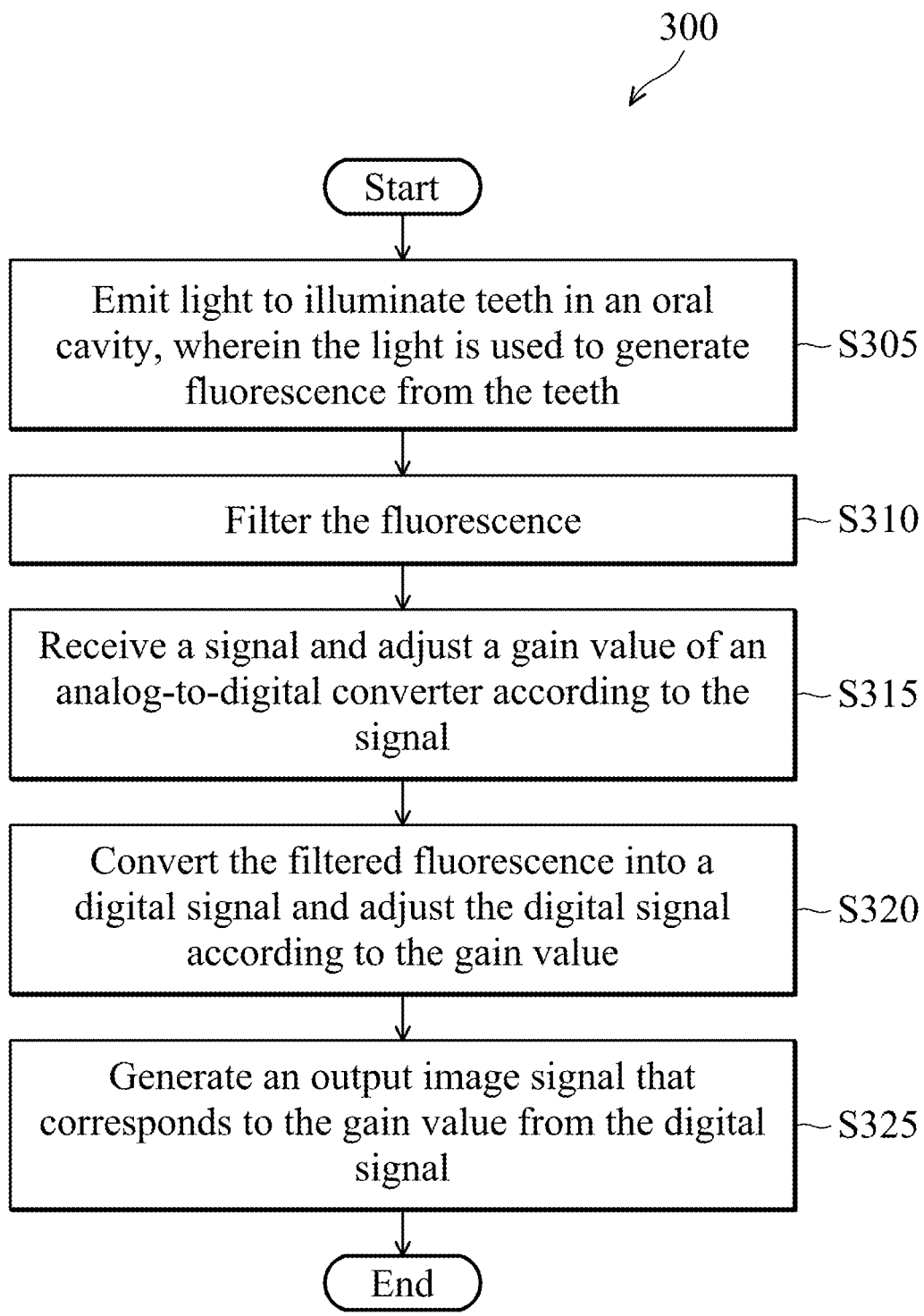
FIG. 3 is a flow diagram illustrating a method for dynamically adjusting fluorescent imaging according to an embodiment of the present disclosure.

FIG. 3 is a flow diagram 300 illustrating a method for dynamically adjusting fluorescent imaging according to an embodiment of the present disclosure. The method is used in the processor of the examining device 120 of FIG. 1.

In step S305, a light emitting diode of the examining device emits light to illuminate teeth in an oral cavity, wherein the light is used to generate fluorescence from the teeth. In step S310, an optical filter of the examining device filters the fluorescence. In an embodiment, the optical filter filters out light including a wavelength band that is less than about 450 nanometers (nm). In another embodiment, the optical filter can filter out light not including wavelength bands selected from the ranges of 430 nm to 480 nm, 620 nm to 750 nm and combinations thereof. In yet another embodiment, the optical filter filters out light not including wavelength bands in the range from 450 nm to 680 nm.

In step S315, an image sensor of the examining device receives a signal and adjusts a gain value of an analog-to-digital converter according to the signal. In an embodiment, the image sensor adjusts the gain value that corresponds to a blue light channel of the analog-to-digital converter according to the signal.

In step S320, the analog-to-digital converter of the examining device converts the filtered fluorescence into a digital signal and adjusts the digital signal according to the gain value. In step S325, a processor of the examining device generates an output image signal that corresponds to the gain value from the digital signal.

Therefore, through the method 300 in FIG. 3, the examining device dynamically adjusts the gain value that corresponds to a blue channel of the analog-digital converter according to the received signal to achieve the effect of dynamically changing the fluorescence imaging.

Figure 4A:
FIGS. 4A-4D are schematic diagrams illustrating different output image signals output by the examining device according to the gain values of different analog-digital converters in accordance with an embodiment of the present disclosure.
Figure 4B:
Figure 4C:
Figure 4D:

FIGS. 4A-4D are schematic diagrams illustrating different output image signals output by the examining device according to the gain values of different analog-digital converters in accordance with an embodiment of the present disclosure. FIG. 4A is an image corresponding to a gain value of 16 of the analog-to-digital converter. FIG. 4B is an image corresponding to a gain value of 9 of the analog-to-digital converter. FIG. 4C is an image corresponding to a gain value of 7 of the analog-to-digital converter. FIG. 4D is an image corresponding to a gain value of 4 of the analog-to-digital converter. As shown in FIGS. 4A-4D, the lower the gain value of the analog-to-digital converter, the lower the ratio of the blue channel in the image.

As shown above, the method and device for dynamically adjusting fluorescent imaging in the present disclosure adjust the gain value of the analog-to-digital converter to dynamically change the proportion of blue light in the fluorescent imaging. In addition, even though the wavelength range of light filtered out by the optical filter is fixed, different fluorescent imaging can be achieved without replacing the optical filter via the method and device for dynamically adjusting fluorescent imaging in the present disclosure.

In addition, in the above exemplary device, although the method has been described on the basis of the flow diagram using a series of steps or blocks, the present disclosure is not limited to the sequence of the steps, and some of the steps may be performed in a different order than that of the remaining steps or may be performed simultaneously with the remaining steps.

In addition, the CPU 214 could execute the program code 218 to perform all of the above-described actions and steps or others described herein.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using another structure, functionality, or structure and functionality in addition to or other than one or more of the aspects set forth herein.

Those with skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those skilled in the art will further appreciate that the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in ways that vary for each particular application, but such implementation decisions should not be interpreted as causing a departure from the scope of the present disclosure.

In addition, the various illustrative logical blocks, modules, and circuits described in connection with the aspects disclosed herein may be implemented within or performed by an integrated circuit ("IC"), an access terminal, or an access point. The IC may comprise a general purpose processor, a digital signal processor (DSP), an application specific integrated circuit (ASIC), a field programmable gate array (FPGA) or another programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general-purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It should be understood that any specific order or hierarchy of steps in any disclosed process is an example of a sample approach. It should be understood that the specific order or hierarchy of steps in the processes may be rearranged while remaining within the scope of the present disclosure. The accompanying method claims present elements of the various steps in a sample order, and are not meant to be limited to the specific order or hierarchy presented.

While the disclosure has been described by way of example and in terms of exemplary embodiment, it is to be understood that the disclosure is not limited thereto. Those who are skilled in this technology can still make various alterations and modifications without departing from the scope and spirit of this disclosure. Therefore, the scope of the present disclosure shall be defined and protected by the following claims and their equivalents.

What is claimed is:

1. A method for dynamically adjusting fluorescent imaging, used in a device, comprising:
    emitting, by a light emitting diode, light to illuminate teeth in an oral cavity, wherein the light is used to generate fluorescence from the teeth;
    filtering, by an optical filter, the fluorescence;
    receiving, by an image sensor, a signal and adjusting a gain value of an analog-to-digital converter according to the signal;
    converting, by the analog-to-digital converter, the filtered fluorescence into a digital signal and adjusting the digital signal according to the gain value; and
    generating, by a processor, an output image signal that corresponds to the gain value from the digital signal,
    wherein the image sensor adjusts the gain value that corresponds to a blue light channel of the analog-to-digital converter according to the signal.

2. The method for dynamically adjusting fluorescent imaging as claimed in claim 1, wherein the optical filter filters out light including a wavelength band that is less than about 450 nanometers (nm).

3. The method for dynamically adjusting fluorescent imaging as claimed in claim 1, wherein the optical filter filters out light not including wavelength bands selected from the ranges of 430 nm to 480 nm, 620 nm to 750 nm and combinations thereof.

4. The method for dynamically adjusting fluorescent imaging as claimed in claim 1, wherein the optical filter filters out light not including wavelength bands in the range from 450 nm to 680 nm.

5. A device for dynamically adjusting fluorescent imaging, comprising:
    a light emitting diode, emitting light to illuminate teeth in an oral cavity, wherein the light is used to generate fluorescence from the teeth;
    an optical filter, filtering the fluorescence;
    an image sensor, coupled to the optical filter and receiving a signal, comprising:
    an analog-to-digital converter, converting the filtered fluorescence into a digital signal; and
    a processor, coupled to the image sensor and generating an output video signal from the digital signal;
    wherein the image sensor adjusts a gain value of the analog-to-digital converter according to the signal, and the analog-to-digital converter adjusts the digital signal according to the gain value, so that the processor generates an output image signal that corresponds to the gain value,
    wherein the image sensor adjusts the gain value that corresponds to a blue light channel of the analog-to-digital converter according to the signal.

6. The device for dynamically adjusting fluorescent imaging as claimed in claim 5, wherein the optical filter filters out light including a wavelength band that is less than about 450 nanometers (nm).

7. The device for dynamically adjusting fluorescent imaging as claimed in claim 5, wherein the optical filter filters out light not including wavelength bands selected from the ranges of 430 nm to 480 nm, 620 nm to 750 nm and combinations thereof.

8. The device for dynamically adjusting fluorescent imaging as claimed in claim 5, wherein the optical filter filters out light not including wavelength bands in the range from 450 nm to 680 nm.

* * * * *